(12) United States Patent
Lai et al.

(10) Patent No.: US 9,879,027 B2
(45) Date of Patent: Jan. 30, 2018

(54) METHOD FOR EXTRACTING HIGH-PURITY ASARININ BY SUPERCRITICAL CARBON DIOXIDE EXTRACTION METHOD AND USE THEREOF

(71) Applicants: THE FIRST AFFILIATED HOSPITAL OF GUANGZHOU MEDICAL UNIVERSITY, Guangzhou (CN); GUANGZHOU INSTITUTE OF RESPIRATORY DISEASE, Guangzhou (CN)

(72) Inventors: Kefang Lai, Guangzhou (CN); Xiaodong Liu, Guangzhou (CN); Bonian Zhong, Guangzhou (CN); Shan Zhong, Guangzhou (CN); Chuqin Huang, Guangzhou (CN)

(*) Notice: Subject to any disclaimer, the term of this patent is extended or adjusted under 35 U.S.C. 154(b) by 12 days.

(21) Appl. No.: 15/494,538

(22) Filed: Apr. 23, 2017

(65) Prior Publication Data

US 2017/0283428 A1  Oct. 5, 2017

Related U.S. Application Data

(63) Continuation of application No. PCT/CN2015/090106, filed on Sep. 21, 2015.

(30) Foreign Application Priority Data

Oct. 30, 2014 (CN) .......................... 2014 1 0606528

(51) Int. Cl.
    A61K 36/00 (2006.01)
    C07D 493/04 (2006.01)
    A61K 36/264 (2006.01)
    A61K 31/36 (2006.01)

(52) U.S. Cl.
    CPC ............ *C07D 493/04* (2013.01); *A61K 31/36* (2013.01); *A61K 36/264* (2013.01); *A61K 2236/13* (2013.01); *A61K 2236/33* (2013.01); *A61K 2236/37* (2013.01); *A61K 2236/39* (2013.01)

(58) Field of Classification Search
None
See application file for complete search history.

*Primary Examiner* — Qiuwen Mi
(74) *Attorney, Agent, or Firm* — Wayne & Ken, LLC; Tony Hom

(57) ABSTRACT

The invention discloses a method for extracting high-purity asarinin and use thereof. The method comprises: putting crude *asarum* powder in an SFE-$CO_2$ device; under the conditions that an extraction kettle has a pressure of 30-40 Mpa and a temperature of 45-70° C., separating kettles I and II have a pressure of 5-10 Mpa, a temperature of 30-50° C. and the flow rate of $CO_2$ is 35-60 L/h, extracting for 60-240 min to obtain total volatile oil of *asarum*; standing the total volatile oil of *asarum* for 24-72 h at a low temperature, and carrying out suction filtration under reduced pressure to obtain crude asarinin; and re-crystallizing the crude asarinin in absolute ethanol twice to obtain pure asarinin. It is found for the first time that asarinin has a good cough-relieving activity and thus can be used in preparing medicines for treating various types of coughs.

7 Claims, 3 Drawing Sheets

METHOD FOR EXTRACTING HIGH-PURITY ASARININ BY SUPERCRITICAL CARBON DIOXIDE EXTRACTION METHOD AND USE THEREOF

TECHNICAL FIELD

The present invention belongs to the technical field of natural medicines, and in particular relates to a method for extracting high-purity asarinin from volatile oil extracted from traditional Chinese medicine *asarum* by an SFE-$CO_2$ method and a use of the asarinin for preparing a medicine for treating cough.

BACKGROUND OF THE PRESENT INVENTION

Cough is a most common chief complaint which troubles outpatients of the respiratory department. Cough is a defensive reflex activity, and physiological cough is a beneficial action. However, long-time frequent or too drastic cough is a pathological reaction, which not only increases the pain of patients, affects rest and sleep and increases physical power consumption, but also promotes the development of diseases and generates other complications when the cough is serious.

*Asarum*, which is a traditional Chinese medicine, has over thousands of years of use history. *Asarum* was initially recorded in *Shennong's Herbal* and was listed in a top grade. *Chinese Pharmacopoeia* (2010) stipulates that *asarum* is derived from dried roots and rootstocks of Aristolochiaceae plant-*Asarum Heterotropoides* Fr. Schmidt var. *mandshuricum* (Maxim.) Kitag., *asarum sieboldii* Miq. var. *seoulense* Nakai or *Asarum sieboldii* Miq, *asarum* is warm in nature, acrid in taste and good for heart, lung and kidney meridians. *Asarum* has effects of relieving exterior syndrome and dispelling cold, dispelling wind and relieving pain, orifice freeing, and warming the lung and dissipating excessive fluid and is used for treating cough and asthma due to phlegm and retained fluid, common cold due to wind-cold, headache, toothache, nasal obstruction and running nose, allergic rhinitis, nasosinusitis and rheumatic arthralgia. A literature has reported that *asarum* volatile oil has an antitussive activity and the main effective component is considered as methyleugenol in the volatile oil (Zhou Huiqiu, *Research on Pharmacological Action of Methyleugenol*, Journal of Chinese Medicine and Pharmacology, 2000, (2):79-80). asarinin is known as a high-content non-volatile constituent in *asarum* (Han Junyan, *Research Progress of Traditional Chinese Medicine asarum*, Chinese Agricultural Science Bulletin, 2011, 27(9):46-50), is mainly contained in Aristolochiaceae plant-*Asarum Heterotropoides* Fr. Schmidt var. *mandshuricum* (Maxim.) Kitag., *Asarum sieboldii* Miq. var. *seoulense* Nakai and *Asarum sieboldii* Miq., and is the quality control component of *asarum* recorded in *Chinese Pharmacopoeia* (2010). The existing literatures report that asarinin is obtained by an extraction method in *Manual of Extraction and Separation of Chemical Components of Traditional Chinese Medicine* edited by Yang Yun in 1998. The method comprises: ethanol-thermal extraction, steam distillation, extraction with diethyl ether, recrystallization with ethanol and the like. Therefore, the process is complex. Meanwhile, heating treatment is needed in the extraction process, which easily causes unstable components of traditional Chinese medicine. Toxic organic reagents, such as $Pb(OAC)_2$, $H_2S$, $ET_2O$ and the like, need to be added in the process, thereby causing the problem of residue of the organic reagents. Therefore, asarinin is not suitable for industrial mass production.

Asarinin is a lignans compound, research reports on asarinin are fewer, and a research has indicated that asarinin has immunosuppressive effect and can be used for antitransplant rejection (Zhang Lili, *Function of Acute Rejection of Heart Transplantation and Influence on Expression of Adhesion Molecules of Asarinin*, China Journal of Chinese Materia Medica, 2006, 31(06):494-497.). The research finds that asarinin has a better antitussive function for a citric acid induced guinea pig cough model; and a research report on an antitussive activity of asarinin has not been seen so far, and a report on a method for preparing asarinin directly from the *asarum* volatile oil by an SFE-$CO_2$ method has also not been seen.

SUMMARY OF THE PRESENT INVENTION

Aiming at the defects in the prior art, the primary purpose of the present invention is to provide a method for extracting high-purity asarinin by an SFE-$CO_2$ method. According to the present invention, the high-purity asarinin (white acicular crystal) is obtained by the following steps: obtaining *asarum* volatile oil by optimizing SFE-$CO_2$ conditions, standing the *asarum* volatile oil at a low temperature, carrying out suction extraction at reduced pressure and recrystallization with absolute ethyl alcohol.

Another purpose of the present invention is to provide a use of the high-purity asarinin obtained by the above method in preparation of medicines for treating various coughs. The effect result of the present invention indicates that, the asarinin has a good antitussive function for a citric acid induced guinea pig cough model and is one of active components of *asarum*, which are used for treating cough.

The purposes of the present invention are realized by the technical solution below:

The method for extracting the high-purity asarinin by the SFE-$CO_2$ method comprises the operating steps below:

(1) washing roots and/or rootstocks of *asarum*, airing and smashing to obtain crude *asarum* powder;

(2) putting the crude *asarum* powder in an extraction kettle of an SFE-$CO_2$ device and sealing; respectively heating the extraction kettle and separating kettles, opening a valve of the extraction kettle when the extraction kettle has a temperature of 45-70° C., and the separating kettles I and II have a temperature of 30-50° C., opening an exhaust valve to empty air when the pressure in the extraction kettle is equal to that of a storage tank, pressurizing a system by a high-pressure pump, and controlling the flow rate of $CO_2$ to 35-60 L/h to start cycling extraction when the extraction kettle has a pressure of 30-40 Mpa, and the separating kettles I and II have a pressure of 5-10 Mpa; and extracting for 60-240 min to obtain total volatile oil of *asarum*;

(3) standing the total volatile oil of *asarum* for 24-72 h at a low temperature of −20-4° C., and carrying out suction filtration at reduced pressure to obtain crude asarinin; and (4) dissolving the crude asarinin with absolute ethyl alcohol having 1-5 times of volume dosage of the crude asarinin, and recrystallizing at a low temperature of −20-4° C. to obtain pure asarinin with a quality purity greater than 98% until white acicular crystals are precipitated.

Te temperature of the extraction kettle in step (2) is set as 50° C.; the extraction kettle has a pressure of 35 Mpa; the separating kettles I and II have a pressure of 5 Mpa and a temperature of 40° C.; the flow rate of $CO_2$ is controlled to 40 L/h; and the extraction time is 180 min.

The *asarum* in step (1) is *Asarum Heterotropoides* Fr. Schmidt var. *mandshuricum* (Maxim.) Kitag., *Asarum sieboldii* Miq. var. *seoulense* Nakai or *Asarum sieboldii* Miq. Preferentially, the *asarum* is *Asarum Heterotropoides* Fr. Schmidt var. *mandshuricum* (Maxim.) Kitag.

The temperature of standing at a low temperature in step (3) is −5° C., and the time of standing at a low temperature is 24 h.

The dosage of the absolute ethyl alcohol in step (4) is 1 time of volume dosage of the crude asarinin.

The times of the recrystallization in step (4) are two.

The use of the high-purity asarinin obtained by the above method in preparation of the medicines for treating various coughs is described as follows: the asarinin is used for preparing the medicines for treating various coughs separately or in combination with other medicines.

The asarinin and usable drug carriers are made into various formulations.

The formulations are granules, tablets, capsules, soft capsules, pills, dripping pills, effervescent tablets, ointments, syrups, injection, oral liquid, mixture, tinctures, sustained-releasing drugs, controlled release drugs or targeting preparations.

The pharmaceutically acceptable carriers are: a filler, a binding agent, a lubricating agent, a disintegrating agent or a wetting agent. The filler comprises lactose, sucrose, corn starch and sorbitol; the binding agent comprises syrup, Arabic gum, gelatin, sorbitol, HPMC (Hydroxypropyl Methyl Cellulose) or PVP (Polyvinylpyrrolidone); the lubricating agent comprises magnesium stearate; the disintegrating agent comprises starch, PVP, crospovidone and microcrystalline cellulose; and the wetting agent is lauryl sodium sulfate.

The asarinin is a lignans compound, has a molecular formula of $C_{20}H_{18}O_6$ and has a chemical formula of 5,5'-[(1R,3aR,4S,6aR)-tetrahydro-1H,3H-furo[3,4-c]furan-1,4-diyl]bis-1,3-Benzodioxole. The structural formula of the asarinin is described as follows:

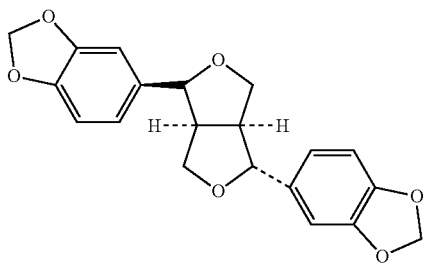

The present invention can adopt a gas chromatographic method or gas chromatography-mass spectrum or an HPLC (High Performance Liquid Chromatography) to measure the content of the *asarum* and the asarinin in the volatile oil of the *asarum*.

The conditions of a gas chromatography are: a DB-5MS quartz capillary column (30 m×0.25 mm×0.25 μm, i.d.) is adopted; the split ratio is 100:1, and the injection volume is 1 μL; the carrier gas is high-purity He; the flow rate is 1 mL·min$^{-1}$; the delay time of solvent is 3 min, the temperature programming: the temperature of the column is risen from 70° C. (6 min) to 100° C. (35 min) at 10° C.·min$^{-1}$ and then is risen to 230° C. (20 min) at 10° C.·min$^{-1}$; and the temperature of an injection port is 250° C.

The conditions of a mass spectrum are: an EI (Electronic Ignition) electron source is adopted, and the carrier gas is He; and the electron energy is 70 eV, the temperature of an ion source is 230° C., the temperature of a transmission line is 250° C., the scanned area is 40-450 m/z, and an NIST (National Institute of Standards and Technology) 2.0 spectrum library.

The conditions of an LC (Liquid Chromatogram) are: an Agilent Zorbax SB-C18 chromatographic column (4.6 mm×250 mm, 5 μm) is adopted; a mobile phase A is water, a mobile phase B is acetonitrile, gradient elution is carried out, and the elution process is: 0-30 min, 45%-60% B, 30-40 min and 60%-100% B; the running time is 40 min, and the balancing time is 10 min; the volume flow rate is 1.0 mL·min$^{-1}$; the detection wavelength is 285 nm; the temperature of the column is 30° C.; and the injection volume is 10 μL.

The effective dosage of the pure asarinin with an antitussive activity of the present invention is 0.35-1.4 g/per man every day for a man having the weight of 60 kg.

The principle of the present invention is described as follows:

Pharmacological experiments prove that, the asarinin prepared by the present invention has a good activity for treating cough and can be used for preventing or treating various coughs.

The results of pharmacodynamic experiments prove that, a guinea pig is taken as a cough model, cough incubation periods of animals can be obviously prolonged through comparison between low, medium and high dosage groups of the asarinin prepared by the present invention and a blank control group after the cough model is simulated by citric acid, thereby reducing the cough times of the guinea pig; compared with the SFE-CO$_2$ volatile oil of the *asarum*, the high dosage group of the asarinin has a better antitussive activity; and the asarinin prepared by a preparation process of the present invention has a better antitussive activity.

The present invention has the beneficial effects that:
(1) the present invention firstly provides a brand-new preparation process of the asarinin, which purifies the asarinin from the volatile oil of the *asarum* obtained by optimizing the SFE-CO$_2$ conditions and has the advantages of simple process, avoidance of oxidation and pyrolysis, no residue of organic solvent, good product quality, high purity, etc.;
(2) the present invention firstly proves that the asarinin has a better antitussive effect, provides a medicine for treating cough, expands the field of selection of antitussive medicines and also makes contribution to the development of the technical field; and
(3) the asarinin prepared by the present invention is a compound having a definite chemical structure and is used for quantizable feeding in medicine preparation, and the content determination and analysis is carried out by the gas chromatographic method or the gas chromatography-mass spectrum or the HPLC to control quality, thereby being conductive to preparing modern dosage forms.

DETAILED DESCRIPTION OF THE PRESENT INVENTION

The present invention is further described below in detail in combination with the drawings and specific embodiments which are not the limit to the present invention.

Embodiment 1

Preparation and Analysis of Asarinin 1.1 Preparation of Asarinin

An extract of total volatile oil of *asarum* is extracted by an SFE-$CO_2$ device, roots and/or rootstocks of *asarum* are washed and aired and are smashed by a smashing machine to obtain crude *asarum* powder, the crude *asarum* powder is added in a charging bottle of an extraction kettle, the charging bottle is put in the extraction kettle, and the extraction kettle is sealed; the extraction kettle and separating kettles are respectively heated, a valve of the extraction kettle is opened when the extraction kettle has a temperature of 50° C., and the separating kettles have a separation temperature of 40° C., an exhaust valve is opened to empty air when the pressure in the extraction kettle is equal to that of a storage tank, a system is pressurized by a high-pressure pump, and the flow rate of $CO_2$ is controlled to 40 L/h to start cycling extraction when the extraction kettle reaches a set pressure of 35 Mpa, and the separating kettles I and II respectively reach a set pressure of 5 Mpa; the extraction temperature is kept to 50° C., and the separating temperature of the separating kettles is kept to 40° C. and the extraction time is kept to 180 min, so as to obtain the total volatile oil of *asarum*, and the yield is 2.5% (mL/g); the total volatile oil of *asarum* stands at a temperature of −5° C. for 24 h, and suction filtration is carried out at reduced pressure, so as to obtain crude asarinin; and the crude asarinin is dissolved in absolute ethyl alcohol having the same volume as the crude asarinin, recrystallization is carried out twice at a low temperature of −20-4° C., pure asarinin is obtained until white acicular crystals are precipitated, and the yield is 1.5% (g/mL).

1.2 Analysis of Volatile Oil of *Asarum* and Asarinin 1.2.1 Conditions of LC

An Agilent 1260 HPLC adopts a Zorbax SB-C18 chromatographic column (4.6 mm×250 mm, 5 μm); a mobile phase A is water, a mobile phase B is acetonitrile, gradient elution is carried out, and the elution process is: 0-30 min, 45%-60% B, 30-40 min and 60%-100% B; the running time is 40 min, and the balancing time is 10 min; the volume flow rate is 1.0 mL·$min^{-1}$; the detection wavelength is 285 nm; the temperature of the column is 30° C.; and the injection volume is 10 μL.

1.2.2 Analysis Result

Figure 1:
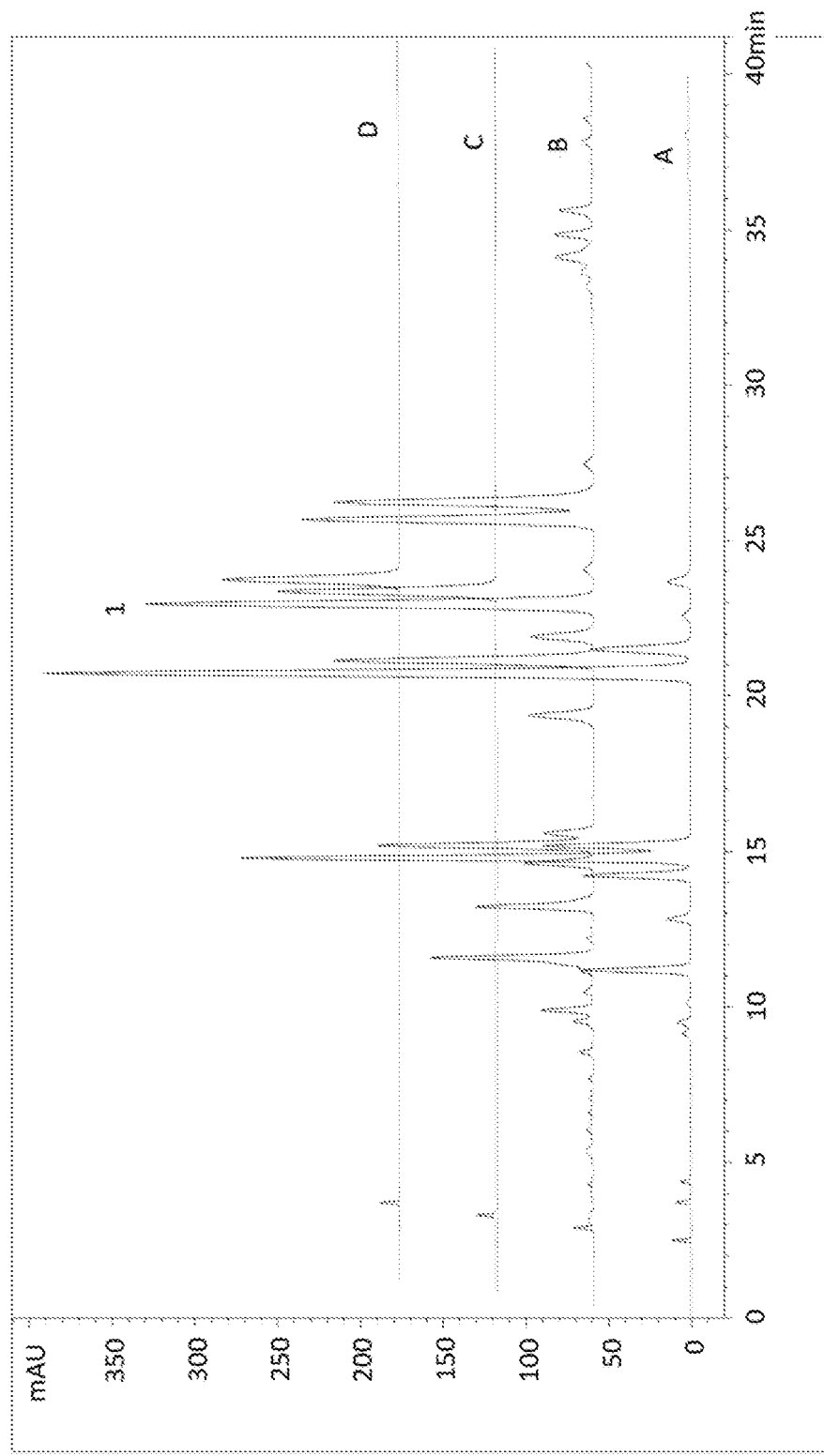
FIG. 1 is an HPLC chromatogram of volatile oil of *asarum* and asarinin, wherein A is conventional volatile oil of *asarum* (obtained by steam distillation); B is total volatile oil of *asarum* (obtained by SFE-CO$_2$); C is pure asarinin (prepared by the present invention); and D is a comparison product of the asarinin.

An analysis result is shown in FIG. 1. It is easily seen from a chromatogram that, compared with conventional volatile oil (SD (Standard Deviation) volatile oil, as shown in FIG. 1A) prepared by steam distillation, the total volatile oil of *asarum* (SFE-$CO_2$ volatile oil, as shown in FIG. 1B) prepared by optimizing SFE-$CO_2$ conditions not only contains all volatile components of the SD volatile oil, but also contains a weak volatile component-asarinin (a chromatographic peak 1). At present, most of literatures indicate that, it is found that the volatile components of the volatile oil obtained by an SD method and an SFE-$CO_2$ method are similar through analysis, and a report that the prepared volatile oil of *asarum* contains non-volatile components such as asarinin has not been seen so far, which indicates that the components of the total volatile oil of *asarum* prepared by the present invention are obviously different from those of volatile oil reported by the existing literatures. The asarinin is a main component of the SFE-$CO_2$ volatile oil prepared by the present invention; a content measuring result indicates that the content of the asarinin in the volatile oil of *asarum* prepared by the present invention is 10.5 wt %; the asarinin (FIG. 1D) is a standard product; the purity of the asarinin (FIG. 1C) prepared by the method of the present invention is measured to be 98% by an area normalization method.

Embodiment 2

Antitussive Function of Asarinin on Cough of Guinea Pigs Induced by Citric Acid 2.1 Experimental Materials Experimental animals: 250-350 g of common level Hartley guinea pigs, including half males and half females are provided by Guangdong Medical Experimental Animal Center, wherein the number of the animal certificate is SCXK (Yue) 2008-0002.

Reagents and instruments: citric acid monohydrate (Guangzhou Chemical Reagent Factory, batch number: 20121001-2), wherein 0.8 M of citric acid solution is prepared by adding normal saline into citric acid monohydrate when in use; an animal noninvasive Buxco lung function detecting system (Buxco Company of America); an Aeroneb Pro atomizer (Aerogen (Ireland) Co., Ltd.); and a gavage needle (Guangdong Medical Experimental Animal Center).

2.2 Experimental Method

A citric acid induced guinea pig cough model is adopted for efficacy evaluation. 112 Hartley guinea pigs are put in a 6 L plethysmograph of the animal noninvasive Buxco lung function detecting system one by one; the air velocity of a drift indicator is 2.5 L/min; 0.8 M of atomized aerosol of citric acid ultrapure aqueous solution is led for 1 min by the Aeroneb Pro atomizer; the average diameter of the atomized granules is 2.5 μm; observation is carried out for 5 min; the sound of cough is recorded and amplified by an indoor microphone; sound waves are analyzed by Biosystem XA software; and computer software is used for processing sound data and recording cough situations. A trained observer observes whether a cough response exists or not, records the cough times within 6 min since atomization and selects the guinea pigs with more than 10 cough times as qualified animals for tests.

56 Hartley guinea pigs qualified by screening, including half males and half females, are randomly divided into 7 groups; 1 mL/100 g of normal saline is provided to a blank control group; a corresponding solvent (Tween-80 aqueous solution with 5% volume concentration) with equal volume is provided to a solvent group; 30 mg/kg of codeine phosphate with equal volume is provided to a positive drug group, asarinin (30 mg/kg, 60 mg/kg and 120 mg/kg of samples in embodiment 1) and total volatile oil of *asarum* (200 mg/kg of samples in embodiment 1) with equal volume are provided to each of administration groups; administration is carried out one time every day for successive 3 days. A citric acid atomization simulation test is carried out in the animal noninvasive Buxco lung function detecting system within 2 h after last administration (atomization conditions are described above); the cough times (N) and the cough incubation periods within 6 min are recorded; and the antitussive ratios of all the administration groups are calculated by a formula: antitussive ratio=($N_{(blank\ control)}$−$N_{(administration\ group)}$/$N_{(blank\ control)}$)×100%.

The data are expressed by x̄±s, and a one-way analysis of variance is carried out on parameters of all the groups by IBM SPSS Statistics 19.0 software.

Figure 2:
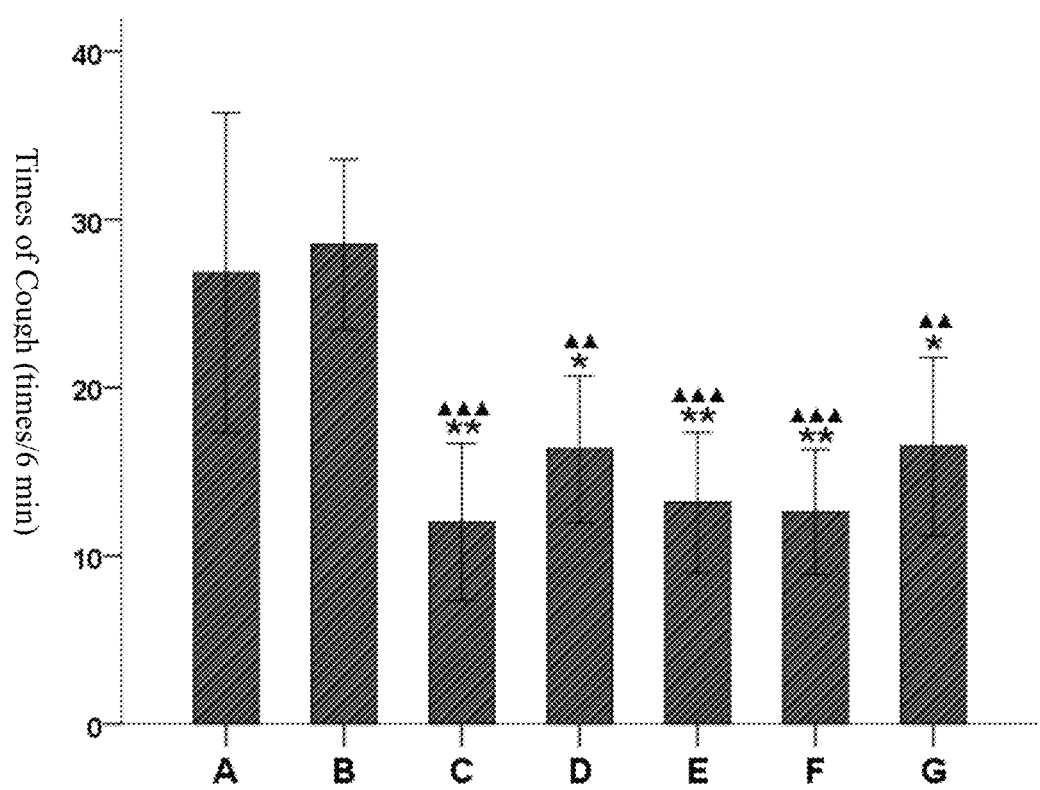
FIG. 2 is the influence ($\bar{x}\pm s$, n=8) of the asarinin on cough times of guinea pigs induced by citric acid, wherein A is a blank group; B is a solvent group (5% Tween-80); C is a codeine phosphate (30 mg/kg) group; D, E and F are asarinin (30, 60 and 120 mg/kg) groups; G is a group of SFE-$CO_2$ volatile oil of *asarum* (200 mg/kg); compared with the blank group, *$p<0.05$, and **$p<0.01$; and compared with the solvent group, ▲▲$p<0.01$, and ▲▲▲$p<0.001$.

2.3 Experimental Result 2.3.1 Influence of Asarinin on Cough Times of Guinea Pigs Induced by Citric Acid The cough times and the cough inhibition ratios within 6 min after all the groups of animals are atomized and simulated by citric acid are shown in Table 1 and FIG. 2. As shown in Table 1 and FIG. 2, compared with the blank group, the cough times of the guinea pigs can be reduced in low, medium and high dosage groups of asarinin and have obvious difference (in the low dosage group: $p<0.05$; and in the medium and high dosage groups: $p<0.01$); the antitussive ratio is 39.2%, 50.7% and 53.0% respectively, wherein the antitussive effect of the high dosage group of asarinin (120 mg/kg) is close to the level of the codeine phosphate (30 mg/kg); and compared with the SFE-$CO_2$ volatile oil of *asarum*, the medium and high dosage groups of asarinin have a better antitussive effect (the antitussive ratio of the SFE-$CO_2$ volatile oil of *asarum* is 38.4%.), but no obvious difference exists among the groups.

The above result indicates that, the asarinin has a good antitussive function and a dosage-effect relationship.

TABLE 1

Influence of Asarinin on Cough Times of Guinea Pigs Induced by Citric Acid (x̄ ± s, n = 8)

| Group | Dosage (mg/kg) | Cough Time (Number of Times) | Antitussive Ratio (%) |
|---|---|---|---|
| Blank Control | — | 26.8 ± 4.8 | — |
| Solvent Control | — | 28.5 ± 2.5 | — |
| Codeine Phosphate | 30 | 12.0 ± 2.3**▲▲▲ | 55.2 |
| Low-dosage Asarinin | 30 | 16.3 ± 2.2*▲▲ | 39.2 |
| Medium-dosage Asarinin | 60 | 13.2 ± 2.1**▲▲▲ | 50.7 |
| High-dosage Asarinin | 120 | 12.6 ± 1.9**▲▲▲ | 53.0 |
| SFE-$CO_2$ Volatile Oil | 200 | 16.5 ± 2.6*▲▲ | 38.4 |

Note:
compared with the blank control group: *$p < 0.05$, and **$p < 0.01$; and compared with the solvent group: ▲▲$p < 0.01$, and ▲▲▲$p < 0.001$.

Figure 3:
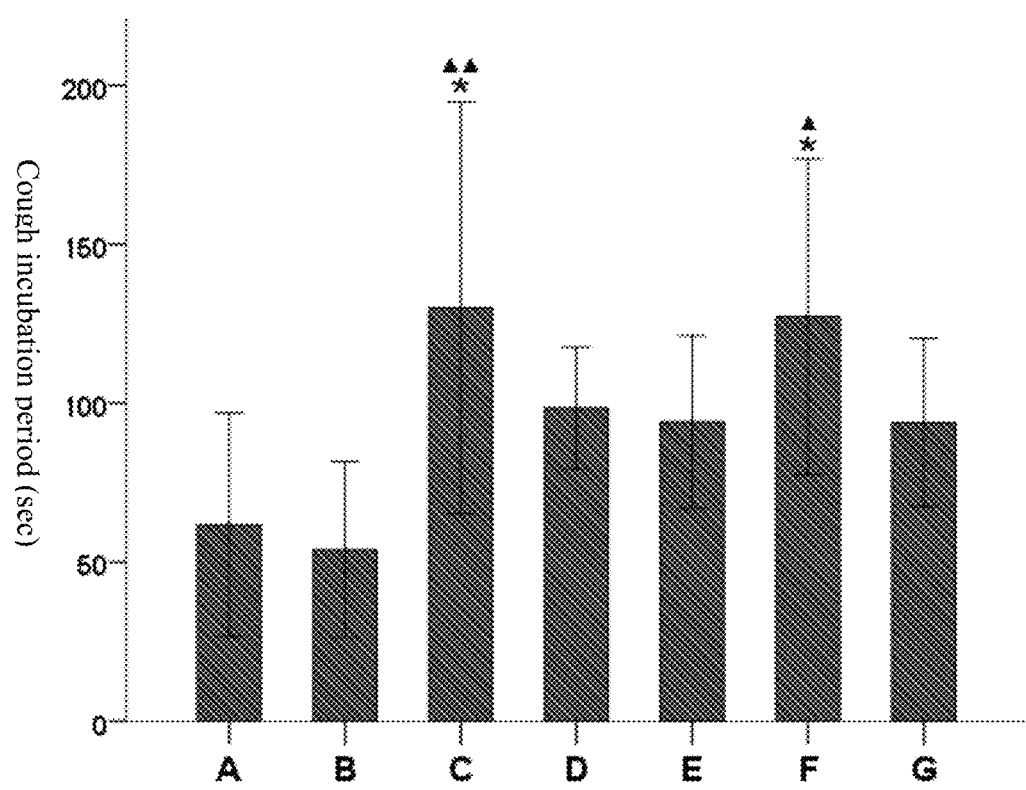
FIG. 3 is the influence ($\bar{x}\pm s$, n=8) of the asarinin on cough incubation periods of the guinea pigs induced by the citric acid, wherein A is a blank group; B is a solvent group (5% Tween-80); C is a codeine phosphate (30 mg/kg) group; D, E and F are asarinin (30, 60 and 120 mg/kg) groups; G is a group of SFE-$CO_2$ volatile oil of *asarum* (200 mg/kg); compared with the blank group, *$p<0.05$; and compared with the solvent group, ▲▲$p<0.01$, and ▲▲▲$p<0.01$.

Cough incubation periods within 6 min after all the groups of animals are atomized and simulated by the citric acid are shown in Table 2 and FIG. 3. As shown in Table 2 and FIG. 3, compared with the blank group, the cough incubation periods of the guinea pigs can be prolonged in the different dosage groups of asarinin, wherein in the high dosage group, $p<0.05$. The function of the high dosage group of asarinin for prolonging the cough incubation periods of the guinea pigs is close to that of the codeine phosphate. Compared with the SFE-$CO_2$ volatile oil of *asarum*, the high dosage group of asarinin has a better function for prolonging the cough incubation periods.

TABLE 2

Influence of Asarinin on Cough Incubation Periods of Guinea Pigs Induced by Citric Acid (x̄ ± s, n = 8)

| Group | Dosage (mg/kg) | Cough Incubation Period (S) |
|---|---|---|
| Blank Control | — | 61.8 ± 17.6 |
| Solvent Control | — | 54.0 ± 13.8 |
| Codeine Phosphate | 30 | 130.0 ± 32.4*▲▲ |
| Low-dosage Asarinin | 30 | 98.5 ± 9.5 |
| Medium-dosage Asarinin | 60 | 94.2 ± 13.6 |
| High-dosage Asarinin | 120 | 127.3 ± 24.8*▲ |
| SFE-$CO_2$ Volatile Oil | 200 | 94.0 ± 13.3 |

Note:
compared with the blank control group: *$p < 0.05$; and compared with the solvent group: ▲$p < 0.05$, and ▲▲$p < 0.01$.

Embodiment 3

The pure asarinin prepared by the method in embodiment 1 is dissolved by adding 5% (volume percent) of Tween-80 aqueous solution, simple syrup is added until the mass content of sugar is more than 50% (mass percent), 3‰ (mass percent) of sodium benzoate and ethylparaben are added and uniformly mixed, the mixture is boiled, filtration is carried out at a high temperature, distilled water is added to a specified amount, and subpackaging is carried out to obtain asarinin cough syrup.

Embodiment 4

The asarinin and aerosol that are prepared by the method in embodiment 1 are sieved by a 60-mesh sieve and then fully and uniformly mixed, magnesium stearate is added, and mixing and dry granulation are carried out. Granules are sieved by a 40-mesh sieve, and filled to obtain capsules.

Embodiment 5

Sesame oil is added into the asarinin prepared by the method in embodiment 1 at a proportion (weight ratio) of 1:0-5 of the asarinin to the sesame oil, the asarinin and the sesame oil are uniformly mixed, and the mixture is taken as a liquid medicine for standby application. One part of gelatin is added into a mixture (preservative) of 0.6-1.2 parts of glycerinum and 0.2% of methylparaben-propyl paraben (the mass ratio is 4:1), the mixture is soaked into 0.7-1.4 volume times of water for more than 2 h, heated and dissolved, pressure is reduced to remove bubbles, and the temperature of the obtained mixture is preserved at 60-65° C. for standby application. The above liquid medicine is put in a pill press, and liquid of the above gelatin is taken as capsule materials and is pressed into soft capsules at a temperature of 45-55° C.

Embodiment 6

Polyvinylpyrrolidone is added into the asarinin prepared by the method in embodiment 1, the mixture is uniformly mixed, granulated, dried and broken, magnesium stearate is added and is uniformly mixed, the obtained mixture is tableted to obtain tablets.

The above specific implementation manners are preferential embodiments of the present invention and cannot limit the present invention. Any other changes or other equivalent replacement manners without departing from the technical solution of the present invention shall be included in the protection scope of the present invention.

What is claimed is:

1. A method for extracting high-purity asarinin by an SFE-$CO_2$ method, characterized in that: the method comprises the operating steps below:

(1) washing roots and/or rootstocks of *asarum*, airing and smashing to obtain crude *asarum* powder;

(2) putting the crude *asarum* powder in an extraction kettle of an SFE-$CO_2$ device and sealing; respectively heating the extraction kettle and separating kettles, opening a valve of the extraction kettle when the extraction kettle reaches a temperature of 45-70° C., and the separating kettles I and II reach a temperature of 30-50° C., opening an exhaust valve to empty air when a pressure in the extraction kettle is equal to that of a storage tank, pressurizing a system by a high-pressure pump, and controlling a flow rate of $CO_2$ to 35-60 L/h to start cycling extraction when the extraction kettle reaches a pressure of 30-40 Mpa, and the separating kettles I and II reach a pressure of 5-10 Mpa; and extracting for 60-240 min to obtain total volatile oil of *asarum*;

(3) standing the total volatile oil of *asarum* for 24-72 h at a low temperature of −20-4° C., and carrying out suction filtration at reduced pressure to obtain crude asarinin; and (4) dissolving the crude asarinin with absolute ethyl alcohol with 1-5 times of volume dosage of the crude asarinin, and recrystallizing at a low temperature of −20-4° C. to obtain pure asarinin with a quality purity greater than 98% until white acicular crystals are precipitated.

2. The method for extracting the high-purity asarinin by the SFE-$CO_2$ method according to claim 1, characterized in that: the temperature of the extraction kettle in step (2) is set as 50° C.;

the extraction kettle reaches a pressure of 35 Mpa; the separating kettles I and II reach a pressure of 5 Mpa and a temperature of 40° C.; the flow rate of $CO_2$ is controlled to 40 L/h; and the extraction time is 180 min.

3. The method for extracting the high-purity asarinin by the SFE-$CO_2$ method according to claim 1, characterized in that: the *asarum* in step (1) is *Asarum Heterotropoides* Fr. Schmidt var. *mandshuricum* (Maxim.) Kitag., *Asarum sieboldii* Miq. var. *seoulense* Nakai or *Asarum sieboldii* Miq.

4. The method for extracting the high-purity asarinin by the SFE-$CO_2$ method according to claim 1, characterized in that: the *asarum* in step (1) is *asarum Heterotropoides* Fr. Schmidt var. *mandshuricum* (Maxim.) Kitag.

5. The method for extracting the high-purity asarinin by the SFE-$CO_2$ method according to claim 1, characterized in that: the temperature of standing at a low temperature in step (3) is −5° C., and the time of standing at a low temperature is 24 h.

6. The method for extracting the high-purity asarinin by the SFE-$CO_2$ method according to claim 1, characterized in that: the absolute ethyl alcohol in step (4) is 1 time of volume dosage of the crude asarinin.

7. The method for extracting the high-purity asarinin by the SFE-$CO_2$ method according to claim 1, characterized in that: the times of the recrystallization in step (4) are two.

* * * * *